United States Patent [19]
Grierson et al.

[11] Patent Number: 5,824,873
[45] Date of Patent: Oct. 20, 1998

[54] TOMATO RIPENING TOM41 COMPOSITIONS AND METHODS OF USE

[75] Inventors: Donald Grierson, Loughborough, United Kingdom; Susan Dale Lawrence, Ithaca, N.Y.; Gloria Andrews Moore, Gainesville, Fla.; Wolfgang Walter Schuch, Crowthorne, United Kingdom

[73] Assignees: University of Florida, Gainesville, Fla.; Zeneca Limited, London, United Kingdom

[21] Appl. No.: 596,111

[22] PCT Filed: Jul. 27, 1994

[86] PCT No.: PCT/GB94/01611

§ 371 Date: Apr. 10, 1996

§ 102(e) Date: Apr. 10, 1996

[87] PCT Pub. No.: WO95/04152

PCT Pub. Date: Feb. 9, 1995

[30] Foreign Application Priority Data

Jul. 30, 1993 [GB] United Kingdom ................. 9315751

[51] Int. Cl.$^6$ .................... A01H 5/00; A01H 5/10; C12N 1/21; C12N 5/14; C12N 15/29; C12N 15/82
[52] U.S. Cl. ................. 800/205; 435/172.3; 435/252.33; 435/320.1; 435/419; 536/23.6; 800/250
[58] Field of Search .................... 536/23.2, 23.6, 536/24.1; 435/320.1, 419, 423, 172.3, 252.33; 47/58; 800/205, DIG. 9, DIG. 52, DIG. 44, 250

[56] References Cited

PUBLICATIONS

Gao J, et al. "The stability of foreign protein production in genetically modified plant cells." Plant Cell Rep. 10: 533–536, 1991.

Liaw G–J, et al. "Characterization of downstream elements in a Raf–1 pathway." PNAS 90: 858–862, Feb. 1993.

Hiatt A, et al. "Production of antibodies in transgenic plants." Nature 342: 76–78, Nov. 2, 1989.

Koziel MG, et al. "Optimizing expression of transgenes with an emphasis on post–transcriptional events." Plant Mol. Biol. 32: 393–405, 1996.

Stam M, et al. "The silence of genes in transgenic plants." Ann. Bot. 79: 3–12, 1997.

Smith CJS, et al. "Antisense RNA inhibition of polygalacturonase gene expression in transgenic tomatoes." Nature 334: 724–726, 1988.

Primary Examiner—Douglas W. Robinson
Assistant Examiner—Amy J. Nelson
Attorney, Agent, or Firm—Arnold, White & Durkee

[57] ABSTRACT

The present invention provides a method for modifying fruit ripening characteristics in plants and is particularly suitable for modification of tomato plants. The DNA expressing an enzyme involved in fruit ripening has been identified and characterized. The DNA is useful in genetically modifying plants to improve shelf life, flavor, resistance to post-harvest pathogens and improved processing characteristics.

16 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1423 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 78..1280

( x i ) SEQUENCE DESCRIPTION: SEQ ID NO:1:

```
CTTCTTGAAA AATGGGGTTG AGGAATTGAA TCATTTGTT CAAATTTTGC TTTTTATTTC        60

ACTTGGAAAC ACAGTAG CTA TGG CTT CCT GTA ATA TTC TTT GTA GTG TCA        110
                    Leu Trp Leu Pro Val Ile Phe Phe Val Val Ser
                     1            5                       10

AAC CCC AAA TTG ATT CTT TTA AAA AGA GTT GTT TTT TTT CAG TCA TGG        158
Asn Pro Lys Leu Ile Leu Leu Lys Arg Val Val Phe Phe Gln Ser Trp
             15                   20                   25

TCA AAT AGG CCA CAT GGT TCA TCC TAT TTT AAC AAG AAT ATT CAA TTT        206
Ser Asn Arg Pro His Gly Ser Ser Tyr Phe Asn Lys Asn Ile Gln Phe
         30                   35                   40

AGA AGA AAC AGT TTT GTT ATT GTG AAG GCT TCA GGT TCA AGA ACT AGT        254
Arg Arg Asn Ser Phe Val Ile Val Lys Ala Ser Gly Ser Arg Thr Ser
     45                   50                   55

AAA AAA CAA GTA GAG ATA ACA TAT AAT CCT GAA GAG AAG TTT AAT AAA        302
Lys Lys Gln Val Glu Ile Thr Tyr Asn Pro Glu Glu Lys Phe Asn Lys
 60                   65                   70                   75

TTA GCT GAT GAA GTG GAT AGA GAA GCT GGG CTT TCA AGA CTC ACT CTT        350
Leu Ala Asp Glu Val Asp Arg Glu Ala Gly Leu Ser Arg Leu Thr Leu
                 80                   85                   90

TTT TCT CCT TGC AAG ATA AAT GTT TTC TTG AGA ATA ACA AGC AAG AGG        398
Phe Ser Pro Cys Lys Ile Asn Val Phe Leu Arg Ile Thr Ser Lys Arg
             95                  100                  105

GAT GAC GGA TAT CAT GAT TTG GCG TCT CTC TTT CAT GTA ATT AGT CTA        446
Asp Asp Gly Tyr His Asp Leu Ala Ser Leu Phe His Val Ile Ser Leu
         110                  115                  120

GGA GAT AAA ATA AAG TTC TCG CTG TCA CCA TCG AAG TCA AAG GAT CGT        494
Gly Asp Lys Ile Lys Phe Ser Leu Ser Pro Ser Lys Ser Lys Asp Arg
     125                  130                  135

TTA TCT ACT AAT GTT GCT GGA GTT CCA CTC GAT GAG AGA AAT CTG ATT        542
Leu Ser Thr Asn Val Ala Gly Val Pro Leu Asp Glu Arg Asn Leu Ile
140                  145                  150                  155

ATA AAG GCC CTC AAT CTT TAT AGG AAA AAG ACT GGA ACA GAC AAT TAC        590
Ile Lys Ala Leu Asn Leu Tyr Arg Lys Lys Thr Gly Thr Asp Asn Tyr
                 160                  165                  170

TTT TGG ATT CAT CTT GAT AAG AAA GTG CCT ACT GGA GCT GGT CTT GGT        638
Phe Trp Ile His Leu Asp Lys Lys Val Pro Thr Gly Ala Gly Leu Gly
             175                  180                  185

GGT GGG AGC AGT AAT GCT GCA ACA ACT CTG TGG GCA GCA AAT CAA TTC        686
Gly Gly Ser Ser Asn Ala Ala Thr Thr Leu Trp Ala Ala Asn Gln Phe
         190                  195                  200

AGT GGT TGT GTT GCC ACT GAA AAG GAG CTC CAA GAG TGG TCT GGT GAG        734
Ser Gly Cys Val Ala Thr Glu Lys Glu Leu Gln Glu Trp Ser Gly Glu
     205                  210                  215
```

-continued

```
ATT GGT TCT GAT ATT CCT TTC TTC TTC TCT CAT GGA GCA GCC TAC TGT      782
Ile Gly Ser Asp Ile Pro Phe Phe Phe Ser His Gly Ala Ala Tyr Cys
220             225                 230                  235

ACG GGT AGG GGT GAG GTT GTT CAG GAT ATC CCG TCA CCC ATA CCA TTT      830
Thr Gly Arg Gly Glu Val Val Gln Asp Ile Pro Ser Pro Ile Pro Phe
                240                 245                  250

GAC ATT CCA ATG GTC CTC ATA AAG CCT CAA CAG GCA TGC TCC ACT GCT      878
Asp Ile Pro Met Val Leu Ile Lys Pro Gln Gln Ala Cys Ser Thr Ala
            255                 260             265

GAA GTT TAC AAG CGT TTT CAG TTG GAT CTG TCT AGT AAG GTT GAT CCC      926
Glu Val Tyr Lys Arg Phe Gln Leu Asp Leu Ser Ser Lys Val Asp Pro
        270                 275             280

TTG AGC TTA CTG GAG AAA ATC TCA ACT AGT GGA ATA TCT CAA GAT GTG      974
Leu Ser Leu Leu Glu Lys Ile Ser Thr Ser Gly Ile Ser Gln Asp Val
    285                 290                 295

TGT GTC AAT GAT TTA GAA CCT CCT GCC TTT GAA GTT CTT CCA TCT CTT     1022
Cys Val Asn Asp Leu Glu Pro Pro Ala Phe Glu Val Leu Pro Ser Leu
300             305                 310                  315

AAA AGG TTA AAA CAA CGA GTA ATT GCT GCT GGC CGA GGA CAA TAT GAT     1070
Lys Arg Leu Lys Gln Arg Val Ile Ala Ala Gly Arg Gly Gln Tyr Asp
                320                 325                  330

GCA GTC TTC ATG TCT GGA AGT GGA AGC ACA ATA GTA GGG GTT GGC TCT     1118
Ala Val Phe Met Ser Gly Ser Gly Ser Thr Ile Val Gly Val Gly Ser
            335                 340             345

CCA GAT CCA CCA CAA TTT GTC TAT GAT GAT GAA GAA TAC AAG GAT GTC     1166
Pro Asp Pro Pro Gln Phe Val Tyr Asp Asp Glu Glu Tyr Lys Asp Val
        350                 355             360

TTC TTG TCA GAA GCA AGT TTC ATC ACT CGA CCA GCC AAC GAG TGG TAT     1214
Phe Leu Ser Glu Ala Ser Phe Ile Thr Arg Pro Ala Asn Glu Trp Tyr
    365                 370                 375

GTT GAA CCT GTT TCA GGT AGC ACT ATT GGT GAT CAA CCT GAG TTC TCT     1262
Val Glu Pro Val Ser Gly Ser Thr Ile Gly Asp Gln Pro Glu Phe Ser
380             385                 390                  395

ACA TCT TTT GAC ATG TCT TAAAAGGCTC AGAAGAGCTG TAAAATTGAA            1310
Thr Ser Phe Asp Met Ser
            400

GCAATAGGAG AAGTTTTTGT TGTAAATGTT ATATCCTATA ATTTCTGTAG TATCATCCTT   1370

TTACTTTGGA TGCACTATTC AAGAAAATAA AATTAGTCAC AATCTGATCG AAA          1423
```

( 2 ) INFORMATION FOR SEQ ID NO:2:

( i ) SEQUENCE CHARACTERISTICS:
        ( A ) LENGTH: 401 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu Trp Leu Pro Val Ile Phe Phe Val Val Ser Asn Pro Lys Leu Ile
 1               5                  10                   15

Leu Leu Lys Arg Val Val Phe Phe Gln Ser Trp Ser Asn Arg Pro His
                20                  25                   30

Gly Ser Ser Tyr Phe Asn Lys Asn Ile Gln Phe Arg Arg Asn Ser Phe
            35                  40                  45

Val Ile Val Lys Ala Ser Gly Ser Arg Thr Ser Lys Lys Gln Val Glu
        50                  55              60

Ile Thr Tyr Asn Pro Glu Glu Lys Phe Asn Lys Leu Ala Asp Glu Val
65                  70                  75                  80

Asp Arg Glu Ala Gly Leu Ser Arg Leu Thr Leu Phe Ser Pro Cys Lys
```

-continued

|  |  |  | 85 |  |  |  |  | 90 |  |  |  |  | 95 |  |
|---|---|---|---|---|---|---|---|---|---|---|---|---|---|---|
| Ile | Asn | Val | Phe 100 | Leu | Arg | Ile | Thr | Ser 105 | Lys | Arg | Asp | Asp | Gly 110 | Tyr | His |
| Asp | Leu | Ala 115 | Ser | Leu | Phe | His | Val 120 | Ile | Ser | Leu | Gly | Asp 125 | Lys | Ile | Lys |
| Phe | Ser 130 | Leu | Ser | Pro | Ser | Lys 135 | Ser | Lys | Asp | Arg | Leu 140 | Ser | Thr | Asn | Val |
| Ala 145 | Gly | Val | Pro | Leu | Asp 150 | Glu | Arg | Asn | Leu | Ile 155 | Ile | Lys | Ala | Leu | Asn 160 |
| Leu | Tyr | Arg | Lys | Lys 165 | Thr | Gly | Thr | Asp | Asn 170 | Tyr | Phe | Trp | Ile | His 175 | Leu |
| Asp | Lys | Lys | Val 180 | Pro | Thr | Gly | Ala | Gly 185 | Leu | Gly | Gly | Gly | Ser 190 | Ser | Asn |
| Ala | Ala | Thr 195 | Thr | Leu | Trp | Ala | Ala 200 | Asn | Gln | Phe | Ser | Gly 205 | Cys | Val | Ala |
| Thr | Glu 210 | Lys | Glu | Leu | Gln | Glu 215 | Trp | Ser | Gly | Glu | Ile 220 | Gly | Ser | Asp | Ile |
| Pro 225 | Phe | Phe | Phe | Ser | His 230 | Gly | Ala | Ala | Tyr | Cys 235 | Thr | Gly | Arg | Gly | Glu 240 |
| Val | Val | Gln | Asp | Ile 245 | Pro | Ser | Pro | Ile | Pro 250 | Phe | Asp | Ile | Pro | Met 255 | Val |
| Leu | Ile | Lys | Pro 260 | Gln | Gln | Ala | Cys | Ser 265 | Thr | Ala | Glu | Val | Tyr 270 | Lys | Arg |
| Phe | Gln | Leu 275 | Asp | Leu | Ser | Ser | Lys 280 | Val | Asp | Pro | Leu | Ser 285 | Leu | Leu | Glu |
| Lys | Ile 290 | Ser | Thr | Ser | Gly | Ile 295 | Ser | Gln | Asp | Val | Cys 300 | Val | Asn | Asp | Leu |
| Glu 305 | Pro | Pro | Ala | Phe | Glu 310 | Val | Leu | Pro | Ser | Leu 315 | Lys | Arg | Leu | Lys | Gln 320 |
| Arg | Val | Ile | Ala | Ala 325 | Gly | Arg | Gly | Gln | Tyr 330 | Asp | Ala | Val | Phe | Met 335 | Ser |
| Gly | Ser | Gly | Ser 340 | Thr | Ile | Val | Gly | Val 345 | Gly | Ser | Pro | Asp | Pro 350 | Pro | Gln |
| Phe | Val | Tyr 355 | Asp | Asp | Glu | Glu | Tyr 360 | Lys | Asp | Val | Phe | Leu 365 | Ser | Glu | Ala |
| Ser | Phe 370 | Ile | Thr | Arg | Pro | Ala 375 | Asn | Glu | Trp | Tyr | Val 380 | Glu | Pro | Val | Ser |
| Gly 385 | Ser | Thr | Ile | Gly | Asp 390 | Gln | Pro | Glu | Phe | Ser 395 | Thr | Ser | Phe | Asp | Met 400 |
| Ser |  |  |  |  |  |  |  |  |  |  |  |  |  |  |  |

TOMATO RIPENING TOM41 COMPOSITIONS AND METHODS OF USE

BACKGROUND OF THE INVENTION

1. Field of the Invention

This application relates to novel DNA constructs, plant cells containing the constructs and plants derived therefrom having modified gene expression.

2. Description of Related Art

The modification of plant gene expression has been achieved by several methods. The molecular biologist can choose from a range of known methods to decrease or increase gene expression or to alter the spatial or temporal expression of a particular gene. For example, the expression of either specific antisense RNA or partial (truncated) sense RNA has been utilised to reduce the expression of various target genes in plants (as reviewed by Bird and Ray, 1991, Biotechnology and Genetic Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, 19:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

SUMMARY OF THE INVENTION

In work leading to the present invention we have identified a gene which expresses an enzyme involved in the ripening of tomatoes. This gene is hereinafter referred to as TOM41.

According to the preset invention there is provided DNA comprising a TOM41 DNA sequence. A TOM41 DNA sequence is any sequence encoding a ripening-related enzyme which is homologous to the sequence shown as SEQ ID NO 1. The DNA sequence may be derived from cDNA, from genomic DNA or may be synthesized ab initio.

A cDNA clone encoding the TOM41 gene product has been obtained from a ripening tomato cDNA library using the method described by Slater et al (1985, Plant Molecular Biology, 5:137–147). The clone pTOM41 includes a sequence coding for substantially the whole of the mRNA produced by the corresponding TOM41 gene.

The mRNA for which pTOM41 codes is expressed in ripening tomato fruit. pTOM41 mRNA was also detected in green fruit but not in ripening fruit of the rin (ripening inhibitor) mutant (Picton PhD Thesis, University of Nottingham 1988). Sequence hybridising to pTOM41 have been located in a single region of chromosome 1 of tomato (Kinzer et al, 1990, Theor Appl Genet, 79:489–496). The biochemical function of the products of these genes has not hitherto been fully elucidated.

The nucleotide sequence of the TOM41 cDNA is given as SEQ ID NO 1. The sequence is 1423 bases in length with a reading frame from 78 to 1280. Searches in DNA data bases indicate that the pTOM41 clone shows homology (50% amino acid sequence homolgy) to an open-reading frame (ORF2) associated with the prs gene of *E. coli* (EMBL Database accession M77237). This open-reading frame forms part of a minor tri-cistronic transcript with the gene for phosphoribosylpyrophosphate synthetase (Post DA et al, 1991, FASEB Journal 5, A812). ORF2 encodes a 31 kD protein the function of which is unknown. Phosphoribosylpyrophosphate acts as a ribosyl donor for synthesis of nucleotides as well as histidine and tryptophan.

The clone pTOM41 was deposited at The National Collections of Industrial and Marine Bacteria (23 St Machar Drive, Aberdeen, Scotland, AB2 1RY) under the terms of the Budapest Treaty on 18 Mar., 1993 under the accession number NCIMB 40543.

An alternative source of the DNA sequence is a suitable gene encoding the TOM41 gene product (the TOM41 enzyme). This gene may differ from the corresponding cDNA in that introns may be present. The introns are not transcribed into mRNA (or, if so transcribed, are subsequently cut out). Oligonucleotide probes or the cDNA clone may be used to isolate the actual TOM41 gene(s) by screening genomic DNA libraries. Such genomic clones may include control sequences operating in the plant genome. Thus it is also possible to isolate promoter sequences which may be used to drive expression of the enzymes or any other protein. These promoters may be particularly responsive to certain developmental events and environmental conditions. The TOM41 gene promoters may be used to drive expression of any target gene.

A TOM41 DNA sequence may be isolated from cDNA or genomic DNA libraries of any suitable plant species using oligonucleotide probes based on the pTOM41 sequence. Bacterial, fungal and algal DNA libraries may also be probed for TOM41 sequences. A TOM41 DNA sequence is any sequence which cross-hybridises with SEQ ID NO 1, preferably having at least 60% homology with SEQ ID NO 1. A TOM41 DNA sequence may encode a protein which is homologous to the predicted gene product encoded by SEQ ID NO 1.

A further way of obtaining a TOM41 DNA sequence is to synthesise it ab initio from the appropriate bases, for example using the appropriate cDNA sequence as a guide.

Some or all of the TOM41 sequence may be incorporated into DNA constructs suitable for plant transformation. These DNA constructs may then be used to modify TOM41 gene expression in plants. "Antisense" or "partial sense" or other techniques may be used to reduce TOM41 gene expression in plant tissue (down-regulation). The levels of expression may also be increased (up-regulation), for example, by incorporation of additional TOM41 genes. The additional genes may be designed to give either the same or different spatial and temporal patterns of expression in the plant.

According to a further aspect of the invention there is provided a DNA construct comprising some or all of a TOM41 DNA sequence under the control of a transcriptional initiation region operative in plants, so that the construct can generate RNA in plant cells.

The fruit-ripening characteristics and related characteristics of plant parts may be modified by transformation with a DNA construct according to the invention. The invention also provides plant cells containing such constructs; plants derived therefrom having modified TOM41 gene expression; and seeds of such plants.

A DNA construct according to the invention may be an "antisense" construct generating "antisense" RNA or a "sense" construct (encoding at least part of the functional enzyme) generating "sense" RNA, "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication WO91/08299) or a sense construct encoding and expressing the functional enzyme may be transformed into the plant to over-express the enzyme.

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable TOM41 sequences is described above. Sequences coding for the whole, or substantially the whole, of the enzyme may thus be obtained. Suitable lengths of this DNA sequences may be cut out for use by means of restriction enzymes. When using genomic DNA as the source of a partial base sequence for transcription it is possible to use either intron or exon regions or a combination of both.

To obtain constructs suitable for modifying expression of TOM41 in plant cells, the cDNA sequence as found in the enzyme cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the enzyme mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional enzyme, the whole of the coding region of the gene is linked to transcriptional control sequences capable of expression in plants.

For example, constructs according to the present invention may be made as follows. A suitable vector containing the desired base sequence for transcription (such as the pTOM41 cDNA clone) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter and the tomato polygalacturonase gene promoter sequence (Bird et al, 1988, Plant Molecular Biology, 11:651–662) or other developmentally regulated fruit promoters. Suitable terminator sequences include that of the *Agrobacterium tumefaciens* nopaline synthase gene (the nos 3' end).

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the TOM41 enzyme (making the DNA construct a full or partial antisense construct).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify enzyme activity only during fruit development and/or ripening. Use of a constitutive promoter will tend to affect enzyme levels and functions in all parts of the plant, while use of a tissue specific promoter allows more selective control of gene expression and affected functions (e.g. fruit colouration). Thus in applying the invention it may be found convenient to use a promoter that will give expression during fruit development and/or ripening. Thus the antisense or sense RNA is only produced in the organ in which its action is required. Fruit development and/or ripening-specific promoters that could be used include the ripening-enhanced polygalacturonase promoter (International Patent Publication Number WO92/08758), the E8 promoter (Diekman & Fischer, 1988, EMBO, 7:3315–3320) and the fruit specific 2A11 promoter (Pear et al, 1989, Plant Molecular Biology, 13:639–651).

The DNA constructs of the invention may be inserted into plants to regulate the expression of the TOM41 gene resulting in modification of plant characteristics (in particular fruit-ripening). Depending on the nature of the construct, the production of the TOM41 gene product may be increased, or reduced, either throughout or at particular stages in the life of the plant. Generally, as would be expected, production of the enzyme is enhanced only by constructs which express RNA homologous to the substantially complete endogenous enzyme mRNAs. Full-length sense constructs may also inhibit enzyme expression. Constructs containing an incomplete DNA sequence shorter than that corresponding to the complete gene generally inhibit the expression of the gene and production of the enzymes, whether they are arranged to express sense or antisense RNA.

A DNA construct of the invention is transformed into a target plant cell. The target plant cell may be part of a whole plant or may be an isolated cell or part of a tissue which may be regenerated into a whole plant. The target plant cell may be selected from any monocotyledonous or dicotyledonous plant species. Plants may be derived from the transformed plant cell by regeneration of transformants and by production of successive generations of the transformants' progeny.

Constructs according to the invention may be used to transform any plant using any suitable transformation technique to make plants according to the invention. Both monocotyledonous and dicotyledonous plant cells may be transformed in various ways known to the art. In many cases such plant cells (particularly when they are cells of dicotyledonous plants) may be cultured to regenerate whole plants which subsequently reproduce to give successive generations of genetically modified plants. Any suitable method of plant transformation may be used. For example, dicotyledonous plants such as tomato and melon may be transformed by Agrobacterium Ti plasmid technology, such as described by Bevan (1984, Nucleic Acid Research, 12:8711–8721) or Fillatti et al (Biotechnology, July 1987, 5:726–730). Such transformed plants may be reproduced sexually, or by cell or tissue culture.

Examples of genetically modified plants according to the present invention include all fruit-bearing plants (such as tomatoes, mangoes, peaches, apples, pears, strawberries, bananas, melons, peppers, chillies, paprika). Other plants that may be modified by the process of the invention include tubers such as radishes, turnips and potatoes, as well as cereals such as maize (corn), wheat, barley and rice. Modified plants may have one or more of the following characteristics:

improved resistance to damage during harvest, packaging and transportation due to slowing of the ripening and over-ripening processes;

longer shelf life and better storage characteristics due to reduced activity of degradative pathways (e.g. cell wall hydrolysis);

improved processing characteristics due to changed activity of enzymes contributing to factors such as: viscosity, solids, pH, elasticity;

improved flavour and aroma at the point of sale due to modification of the sugar/acid balance and other flavour and aroma components responsible for characteristics of the ripe fruit;

modified colour due to changes in activity of enzymes involved in the pathways of pigment biosynthesis (e.g. lyoopene, b-carotene, chalcones and anthocyanins);

increased resistance to post-harvest pathogens such as fungi.

Use of the TOM41 constructs allows modification of TOM41 enzyme activity and thus provides a method for modification of plant characteristics, particularly fruit-ripening. The overall level of TOM41 enzyme activity and the relative activities of other enzymes affect plant development and thus determine certain characteristics of the plant parts. Modification of TOM41 enzyme activity can therefore be used to modify various aspects of plant (including fruit) quality. The activity levels of the enzyme may be either increased or reduced during development depending on the characteristics desired for the modified plant. The TOM41 gene may also be expressed in cells, tissues and organisms that do not normally produce the TOM41 enzyme.

TOM41 gene expression (and hence plant characteristics) may be modified to a greater or lesser extent by controlling the degree of the sense or antisense mRNA production in the plant cells. Thus may be done by suitable choice of promoter sequences, or by selecting the number of copies or the site of integration of the DNA sequences that are introduced into the plant genome. For example, the DNA construct may include more than one TOM41 DNA sequence or more than one recombinant construct may be transformed into each plant cell.

It is also possible to modify TOM41 enzyme activity while also modifying the activity of one or more other enzymes. For example, the other enzymes may be involved in cell metabolism or in fruit development and ripening. Cell wall metabolising enzymes that may be modified in combination with TOM41 include but are not limited to: pectin asterase, polygalacturonase, β-galactanase, β-glucanase. Other enzymes involved in fruit development and ripening that may be modified in combination with TOM41 include but are not limited to: ethylene biosynthetic enzymes, carotenoid biosynthetic enzymes, carbohydrate metabolism enzymes including invertase.

Several methods are available for modification of the TOM41 enzyme activity in combination with other enzymes. For example, a first plant may be individually transformed with a TOM41 construct and then crossed with a second plant which has been individually transformed with a construct encoding another enzyme. As a further example, plants may be either consecutively or co-transformed with TOM41 constructs and with appropriate constructs for modification of the activity of the other enzyme(s). An alternative example is plant transformation with a TOM41 construct which itself contains an additional gene for modification of the activity of the other enzyme(s). The TOM41 constructs may contain sequences of DNA for regulation of the expression of the other enzyme(s) located adjacent to the TOM41 sequences. These additional sequences may be in either sense or antisense orientation as described in International patent application publication number WO93/23551 (single construct having distinct DNA regions homologous to different target genes). By using such methods, the benefits of modifying the TOM41 enzyme activity may be combined with the benefits of modifying the activity of other enzymes.

According to a third aspect of the invention, there is provided a method for modifying TOM41 gene expression in plants by transforming plants with TOM41 DNA constructs and growing such transformed plants or their descendants followed by selection of plants having modified TOM41 gene expression. Suitable TOM41 DNA constructs may be adapted to enhance the production of the TOM41 enzyme or to inhibit such production by the plant when compared with untransformed plants.

This method may be used for modifying fruit-ripening characteristics: fruit-bearing plants are transformed with TOM41 DNA constructs, the transformed plants or their descendants are grown and plants having modified fruit-ripening characteristics are selected.

In this way, plants can be generated which have modified fruit-ripening characteristics due to promotion or inhibition of TOM41 gene expression. Similar modifications may be possible using traditional plant breeding techniques, but the present invention provides a means of transferring the trait into elite lines without a prolonged breeding programme which might alter other traits at the same time. As already discussed, plants produced by the method of the invention may also contain other recombinant constructs, for example constructs having other effects on fruit ripening (such as constructs inhibiting the production of polygalacturonase or pectinesterase, or interfering with ethylene production).

Fruit containing both types of recombinant construct may be made either by successive transformations, or by crossing two varieties that each contain one of the constructs and selecting among the progeny for those that contain both.

DESCRIPTION OF PREFERRED EMBODIMENTS

The invention will now be described by way of example only, with reference to the sequence listing in which:

SEQ ID NO 1 shows the nucleotide sequence of TOM41 cDNA.

EXAMPLE 1
Construction of pPS41: a Sense RNA Vector with the CaMV 35S Promoter The vector pPS41 was constructed using the sequences corresponding to a fragment of the insert of pTOM41 from base 15 to base 1011. This 996 bp fragment was synthesized by polymerase chain reaction using synthetic oligonucleotide primers which incorporated a KpnI site at the 5' end and a XbaI site at the 3' end of the fragment. The PCR fragment was digested with KpnI and XbaI and cloned into the plant transformation vector pJR1Ri which had previously been digested with the same restriction enzymes. pJR1Ri is a derivative of pJR1 (Smith et al, 1988, Nature, 334:724–726) which is a Bin19 based vector (Bevan, 1984, Nucleic Acids Research, 12:8711–8721). This vector permits the expression of the partial sense RNA under the control of the CaMV 35 promoter. The vector includes the a nopaline synthase (nos) 3' end termination sequence.

After synthesis of pPS41, the structure and sense orientation of the TOM41 fragment was confirmed by DNA sequence analysis.

EXAMPLE 2
Construction of a Sense RNA Vector with the Polygalacturonase Promoter The fragment of TOM41 cDNA that was described in Example 1 is also cloned into the vector pJR3 in the sense orientation to give pJR341S. pJR3 is a Bin19 based vector, which permits the expression of the antisense RNA under the control of the fruit-enhanced tomato polygalacturonase (PG) promoter. This vector includes approximately 5 kb of promoter sequence and 1.8 kb of 3' sequence from the PG promoter separated by a multiple cloning site.

After synthesis, the vectors with sense orientation of pTOM41 sequence are identified by DNA sequence analysis.

EXAMPLE 3
Construction of Antisense RNA Vectors with the CaMV 35S Promoter (A) The vector pJR141A is constructed using a sequence corresponding to a fragment of the insert of pTOM41, synthesised by polymerase chain reaction using synthetic primers. The ends of the fragment are made flush with T4 polymerase and it is cloned into the vector pJR1 which has previously been cut with SmaI. pJR1 (Smith et al, 1988, Nature, 334:724–726) is a Bin19 (Bevan, 1984, Nucleic Acids Research, 12:8711–8721) based vector, which permits the expression of the antisense RNA under the control of the CaMV 35S promoter. This vector includes a nopaline synthase (nos) 3' end termination sequence. After synthesis of the vector, the structure and antisense orientation of the sequences are confirmed by DNA sequence analysis.

(b) Another vector is constructed using sequences corresponding to a restriction fragment obtained from pTOM41 and is cloned into the vectors GA643 (An et al, 1988, Plant Molecular Biology Manual A3: 1–19) or pDH51 (Pietrzak et al, 1986, Nucleic Acids Research, 14:5875–5869) which have previously been out with a compatible restriction enzyme(s). A restriction fragment from the pTOM41/pDH51 clone containing the promoter, the pTOM41 fragment and other pDH51 sequence is cloned into SLJ44026B or SLJ44024B (Jones et al, 1990, Transgenic Research, 1) or a Bin19 (Bevan, 1984, Nucleic Acids Research, 12:8711–8721) which permits the expression of the antisense RNA under control of the CaMV 35S promoter. After synthesis of the vector, the structure and antisense orientation of the sequences are confirmed by DNA sequence analysis.

EXAMPLE 4

Construction of Antisense RNA Vectors with the Polygalacturonase Promoter

The fragment of the TOM41 cDNA described in Example 3 is also cloned into the vector pJR3 to give pJR341A. After synthesis, vectors with the correct antisense orientation of TOM41 sequences are identified by DNA sequence analysis.

EXAMPLE 5

Construction of a TOM41 Over-Expression Vector using the CaMV35S Promoter.

The complete sequence of TOM41 cDNA is inserted into the vectors described in Examples 1 or 3.

EXAMPLE 6

Construction of a TOM41 Over-Expression Vector using the Polygalacturonase Promoter.

The complete sequence of TOM41 cDNA is inserted into the vectors described in Examples 2 or 4.

EXAMPLE 7

Generation of Transformed Plants

Vectors are transformed to *Agrobacterium tumefaciens* LBA4404 (a micro-organism widely available to plant biotechnologists) and are used to transform tomato plants.

Transformation of tomato stem segments follow standard protocols (e.g. Bird et al, 1988, Plant Molecular Biology, 11:651–662). Transformed plants are identified by their ability to grow on media containing the antibiotic kanamycin. Plants are regenerated and grown to maturity.

Ripening fruit are analysed for modifications to their ripening characteristics.

The sense RNA vector pPS41 (Example 1) has been transformed into tomato plants (cv. Ailsa craig). At least twenty-two transformants have been generated for analysis.

What is claimed is:

1. A nucleic acid segment comprising an isolated TOM41 gene encoding a polypeptide having the amino acid sequence of SEQ ID NO:2.

2. The nucleic acid segment of claim 1 that has the sequence of SEQ ID NO:1.

3. An isolated nucleic acid segment that encodes a polypeptide comprising the amino acid sequence of SEQ ID NO:2.

4. The nucleic acid segment of claim 3 wherein the encoded polypeptide has the amino acid sequence of SEQ ID NO:2.

5. A DNA segment comprising the nucleic acid segment of claim 1 operatively positioned under the control of a promoter.

6. A DNA segment comprising the nucleic acid segment of claim 1 wherein the DNA is positioned in reverse orientation under the control of a promoter that directs expression of an antisense product.

7. The DNA segment of claim 5 or claim 6 further defined as an expression vector.

8. A vector comprising the nucleic acid segment of claim 1.

9. A host cell transformed with the DNA segment of claim 5 or claim 6.

10. The host cell of claim 9 wherein the host cell is a plant cell.

11. The host cell of claim 10 wherein the host cell is a dicotyledonous plant cell.

12. A method of producing a polypeptide comprising introducing the nucleic acid segment of claim 1 into a host cell and collecting the polypeptide expressed by said cell.

13. A transgenic plant that has incorporated into its genome a transgene that encodes a plant ripening enzyme comprising the amino acid sequence of SEQ ID NO:2.

14. Progeny of the plant of claim 13.

15. Seeds from the plant of claim 13.

16. An *E. coli* cell having NCIMB Accession Number 40543.

* * * * *